United States Patent
Bååth (10) Patent No.: US 6,244,743 B1
(45) Date of Patent: Jun. 12, 2001

(54) METHOD FOR MEASURING TEMPERATURE, MOLECULAR COMPOSITION OR MOLECULAR DENSITIES IN GASES

(76) Inventor: Lars B. Bååth, Blindskärvägen 11, S-439 92 Onsala (SE)

( * ) Notice: Subject to any disclaimer, the term of this patent is extended or adjusted under 35 U.S.C. 154(b) by 0 days.

(21) Appl. No.: 09/595,957

(22) Filed: Jun. 19, 2000

Related U.S. Application Data (63) Continuation of application No. 09/152,853, filed on Sep. 14, 1998, now Pat. No. 6,084,415, which is a continuation of application No. 08/510,444, filed on Aug. 2, 1995, now Pat. No. 5,829,877, which is a continuation-in-part of application No. PCT/SE94/00100, filed on Feb. 3, 1994.

(30) Foreign Application Priority Data

Feb. 3, 1993 (SE) ................................................ 9300347

(51) Int. Cl.$^7$ ............................ G01K 1/14; G01K 13/02; G01J 5/02; G01N 25/00
(52) U.S. Cl. .................... 374/142; 374/45; 374/120; 374/161; 324/637; 324/639
(58) Field of Search ............................ 374/45, 142, 120, 374/161; 324/639, 637, 640, 641; 436/181; 422/83

(56) References Cited

U.S. PATENT DOCUMENTS

| | | | |
|---|---|---|---|
| 2,703,079 | 3/1955 | Argento | 600/531 |
| 3,216,661 | 11/1965 | Sawyer | 236/15 E |
| 3,265,873 | 8/1966 | Sawyer | 327/105 |
| 3,448,380 | 6/1969 | Harrington | 324/639 |
| 3,866,118 | 2/1975 | Ghosh et al. | 324/639 |
| 4,369,040 | 1/1983 | Flygare et al. | 324/636 |
| 4,552,151 | 11/1985 | Bolomey et al. | 128/653 |
| 4,986,654 | 1/1991 | Meijer et al. | 374/161 |
| 5,124,653 | 6/1992 | Andresen et al. | 324/636 |
| 5,551,780 | 9/1996 | Wintrich et al. | 374/45 |
| 5,715,819 | 2/1998 | Svenson et al. | 128/653 |
| 5,826,984 | 10/1998 | Fima | 374/120 |
| 5,841,288 | 11/1998 | Meaney et al. | 324/639 |

OTHER PUBLICATIONS

Townes and Schawlow, "Microwave Spectroscopy," New York, 1995, pp. 486–498.
Millen, D.J., "Microwave Spectroscopy," IEE paper no. 3331 E, Jan 1961, pp. 111–119.
G. Winnewisser, "Spectroscopy in the terahertz region," Vibrational Spectroscopy, 8 (1995) 241–253.

*Primary Examiner*—Diego Gutierrez
*Assistant Examiner*—Stanley J. Pruchnic, Jr.
(74) *Attorney, Agent, or Firm*—Nils H. Ljungman & Associates (57) ABSTRACT

A measuring technique and method are provided to simultaneously determine the molecular density of several molecular species and the temperature within a closed process room in a melting or combustion process. In such processes in the industry, e.g. in metallurgic process industry, it is important to determine the temperature and the contents within the gas or flame without physically connect to or disturb the process. This has shown to raise large problems especially at high temperatures. The radio signal over a frequency band is measured on the outside of the process room through a window in the mantel covering as a function of frequency and registered on a computer as a radio spectrum. The system is calibrated by using a known signal transmitted through the process room. The spectral lines are identified by their frequency from a database. The temperature is determined from several lines of the same molecular specie and the molecular densities are determined from the intensities of the lines. The method is suitable to determine vibrational and rotational excitation of molecular species in the radio wavelength range of 30 micrometers to 500 meters. The densities of molecular species and the temperature can be imaged in three dimensions inside the process room or exhaust channel if interferometers are used for simultaneous two dimensional imaging from several azimuth directions.

20 Claims, 6 Drawing Sheets

METHOD FOR MEASURING TEMPERATURE, MOLECULAR COMPOSITION OR MOLECULAR DENSITIES IN GASES

CONTINUING APPLICATION DATA

This is a continuation of U.S. Ser. No. 09/152,853, filed on Sep. 14, 1998, now U.S. Pat. No. 6,084,415, which is a continuation of U.S. Ser. No. 08/510,444, filed on Aug. 2, 1995, now U.S. Pat. No. 5,829,877, which claims continuation-in-part status from International Application No. PCT/SE94/00100, filed Feb. 3, 1994, and which claims priority from Swedish Patent Application No. 900347-3, filed Feb. 3, 1993. International Application No. PCT/SE94/00100 was pending as of the filing date of the present U.S. application and the U.S. was an elected state in the International Application No. PCT/SE94/00100.

1. FIELD OF THE INVENTION

The invention relates to a method for measuring temperature, molecular densities and molecular composition or any combination thereof, in gases and/or flames in melting and/or combustion processes.

2. BACKGROUND OF THE INVENTION

Conventional gas analysis methods using IR-paramagnetic and mass-spectrometer technology need a physical contact with the gas to be analyzed. This means that the gas has to be cooled before entering the analyzer which may affect the results of the measurements. Another disadvantage with conventional gas analyzers is that they can not simultaneously measure the temperature of the gas and analyze the gas.

It is known that the attenuation of a continuum radio signal can be used to recover the amount of black smoke in exhaust fumes, JP 60-64234. This patent method does not determine any molecular content, nor does it determine any temperature.

It is also known that the changes in the refractive index of flying ash can be used to determine the carbon content therein, WO 90/03568. This patent method does not distinguish between molecular species and does not measure any spectral lines or determine molecular densities, configuration, or temperature.

It is also known that attenuation and reflection in the exhaust fumes from a reaction engine can be used to determine changes in the exhaust fume composition, WO 90/03568. This method does not determine any molecular species or temperature.

It is also known that the existence of a specific molecular specie can be decided if the molecular gas is first mixed with a drive gas and then injected into a cavity chamber, U.S. Pat. No. 5,124,653. The cavity is then adjusted to the wavelength of the molecular transition and the molecular gas is excited by injecting a radio signal. The radio transmitter is then turned off and the molecule will emit at its specific frequency if it is present. This method measures a single molecular line at the time and can only detect the molecular species for which it is specifically adjusted. This method does not measure the temperature or the molecular density within the process since the molecular gas has to be taken out of the process-room to the special cavity and the gas is also contaminated with a drive gas.

None of the above patents discloses discusses, or makes possible the simultaneous determination of a multiple of molecular lines and species or can determine molecular densities and temperature in a working melting process of combustion process without any interaction with the gas flow.

Changes in the pattern of electromagnetic wave fronts represent the most sensitive probes in physics. Electromagnetic waves may penetrate media of varying physical properties, changing its amplitude and phase in a way which is specific to the content of the media. Thus molecular gas will emit or absorb electromagnetic radiation mainly depending on its density, the physical temperature, or the radiation field in the area where the gas resides. Continuum radiation will also be affected when penetrating a media in the sense that the amplitude will be attenuated and the propagation velocity will change, resulting in a sudden change of phase in the interface area. The radioband is of particular interest in that here waves can penetrate deeper into dusty areas and also detect and measure complicated molecules by their rotational transitions.

OBJECT OF THE INVENTION

It is an object of the invention to provide an accurate and reliable method to analyze a gas and to determine the temperature of a gas directly in an industrial process without physical contact with the gas that is being analyzed and without disturbing the gas and the process.

BRIEF DESCRIPTION OF THE DRAWINGS

The invention will be described more closely with reference to the drawings.

DESCRIPTION OF THE PREFERRED EMBODIMENTS

Each molecular species has its own fingerprint in the form of a spectrum of lines, in the radio domain mainly determined by the quantified transitions between vibrational- and/or rotational states. Molecular lines in the atmosphere are very much broadened due to the relatively high pressure. The most significant exception is if the molecular flow is highly directive, e.g. if we are looking through the flow at an angle perpendicular to that of the flow. In that case the pressure broadening will be much less and molecular lines can be well separated. This exception is the case for the gas flow in chimneys or through the gas flow from any burning process if viewed across the flow.

Figure 1:
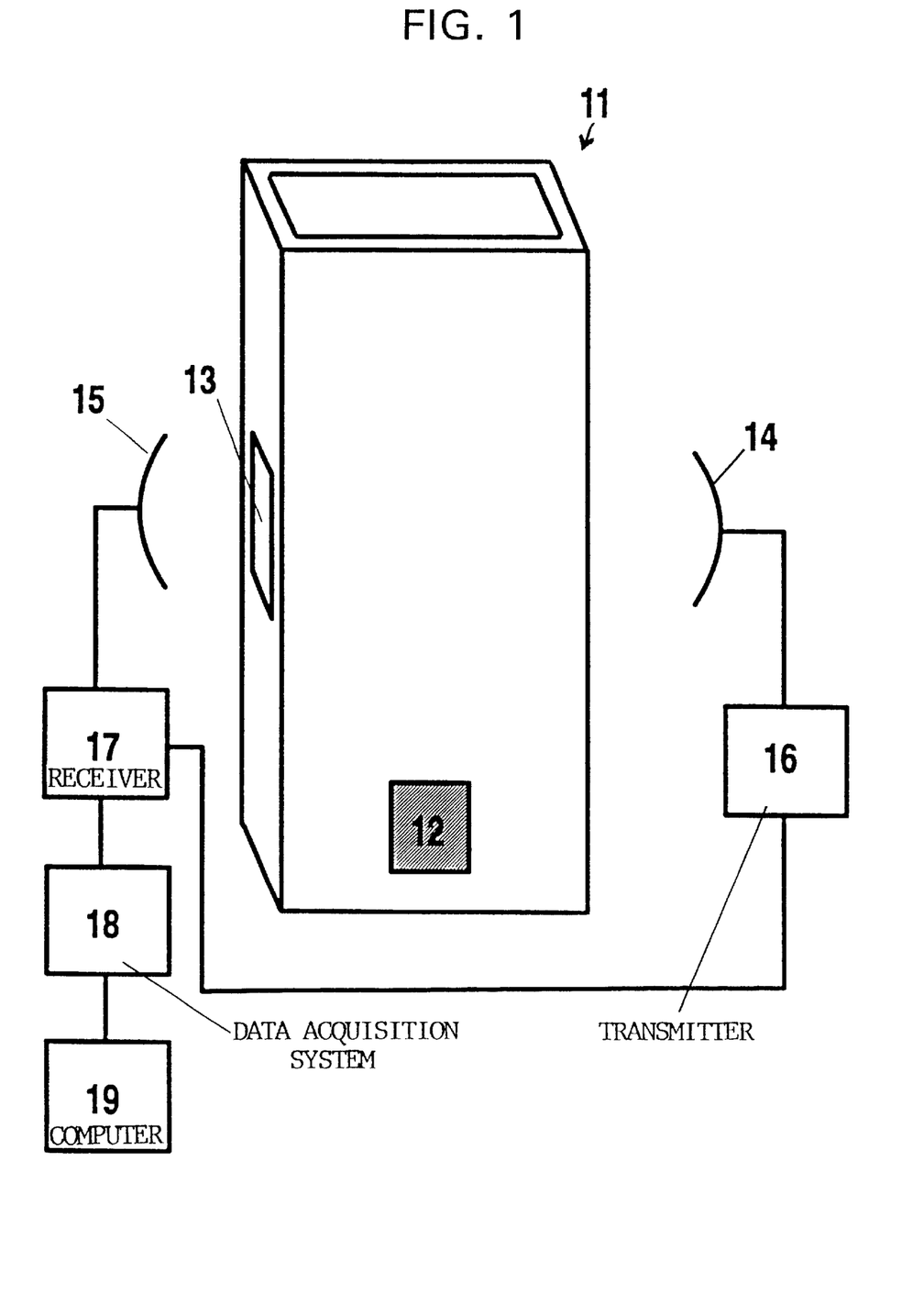
FIG. 1 shows an experimental set up.

The invention can be best described with an experimental set-up shown in FIG. 1. Here a chimney (11) is made out of ceramic material, chrome-magnesite and charmotte, and covered with steel. The chimney has an opening (12) for an oil burner. The steel cover has two opposite windows (13), with intact ceramic material. Outside the windows (13) and in line with the windows are two parabolic antennas (14,15). One of the parabola is connected to a transmitter (16) and the other parabola (15) is connected to a receiver (17). The transmitter consists of a signal generator which is stepped in frequency over a wide frequency band. The received signal is compared with the transmitted signal in a cross-correlator (18) connected to a computer (19).

The received signal consists of a number of spectral lines emitted from the gas inside the chimney overlaid on the background transmitted signal. The transmitted signal is used to calibrate the frequency response of the system and the attenuation through the chimney walls by looking at the received signal between the molecular lines. This baseline will then be subtracted from the received signal and the intensities of the molecular spectral lines can be determined as calibrated inside the chimney.

The system is further calibrated by measuring the signal transmitted through the chimney as a function of frequency when the chimney is empty.

The registered spectrum is stored in a computer. A database is searched for known lines which coincide in frequency with maxima within 'the observed' spectrum. Thereafter a Gaussian model fit is made to the line in order to determine the amplitude, frequency, and line width. A line is considered to be detected if the amplitude of the Gaussian fitted line is more than three times the calculated noise level. The measured amplitudes are then calibrated to an absolute temperature scale.

If a number of lines from the same molecular specie can be detected, then the relative population of the various energy levels may be determined. This relation is mainly determined by the physical temperature of the gas and the density of the molecular specie as: $N_u/g_u = N_{tot}/G(T_{tot})c^{-E_u/T_{tot}}$ where $N_u$ is the number of molecules in the upper energy level of the transition, $g_u$ is the statistical weight of the transition, $E_u$ is the energy of the upper energy level in Kelvin, Q is the rotational constant, $T_{tot}$ is physical temperature, in the case of burning processes where the excitation is dominated by collisions due to the high temperature, and $N_{tot}$ is the column density of the molecules of this particular specie. $N_u/g_u$ is directly proportional to the intensity integrated over the spectral line and can therefore be measured. If a number of spectral lines from a molecule are available, then both the density (if the path length is known) and the physical temperature (if the molecule is predominantly collision excited) can be determined simultaneously. If lines from other molecules are also present, then also the densities of these molecules may be measured from the intensity of a single molecular line.

Figure 2:
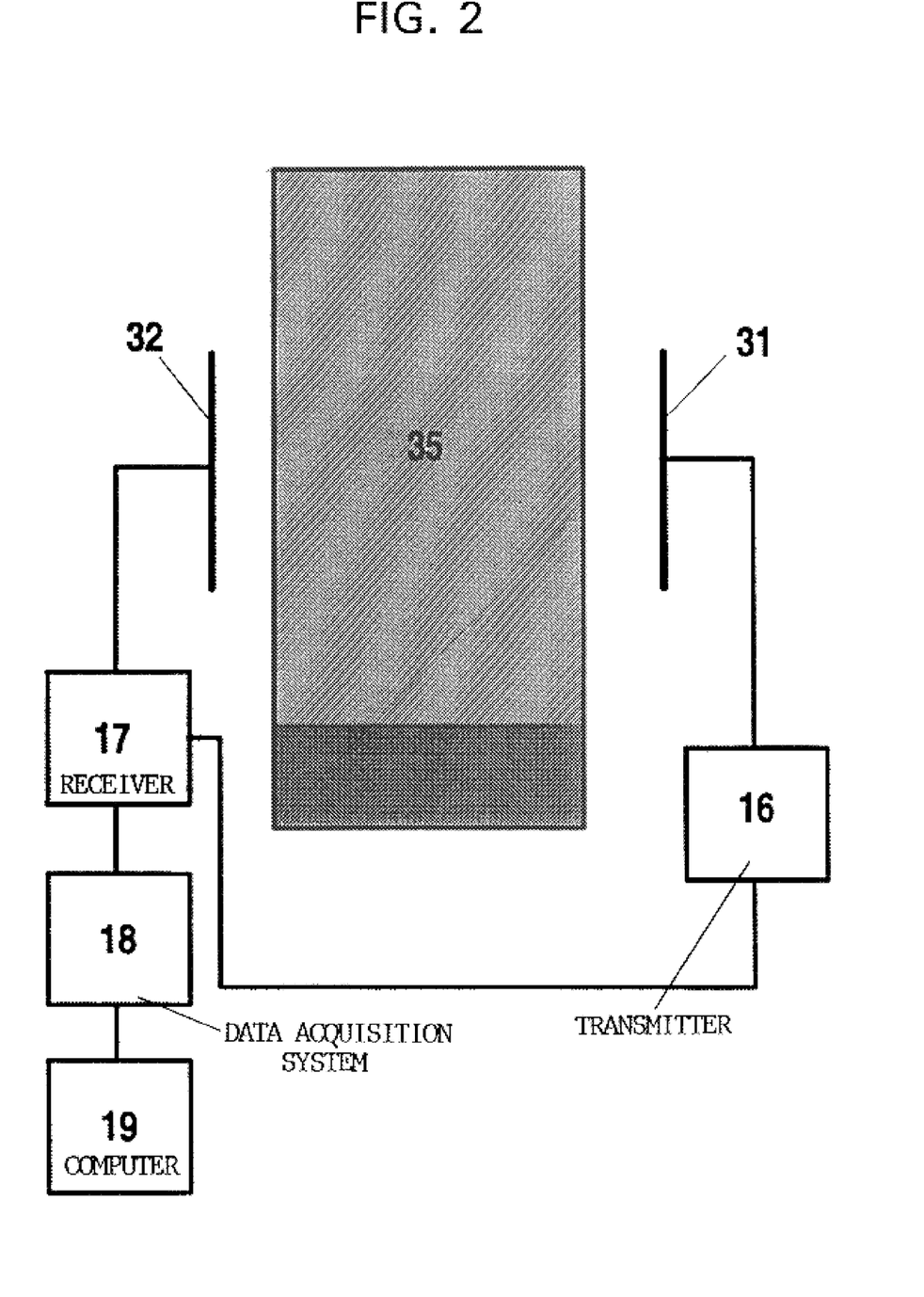
FIG. 2 shows schematically a more sophisticated apparatus.

The radio antenna can also consist of an interferometer where the elements are radio horn antennas mounted in a plane (31,32) and with properly adjusted delay lines as shown in FIG. 2. Then the two dimensional distribution of molecular densities and temperature can be reconstructed by transforming from the aperture (u,v) plane to the image plane.

Figure 3:
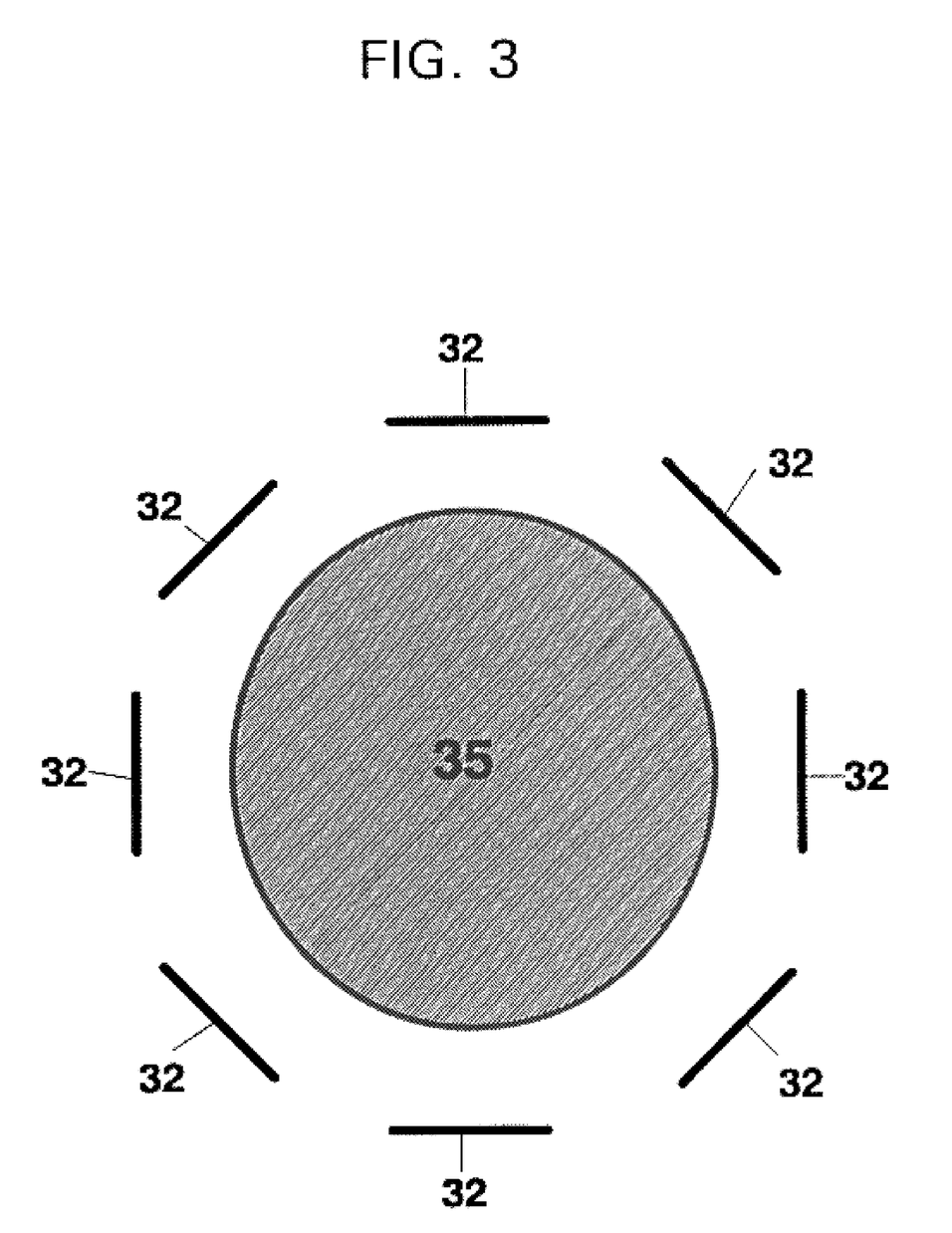
FIG. 3 is a top view of the apparatus in FIG. 2.

If then the system consists of interferometers (32) which are looking into the process room or exhaust channel 35 from different angles as is shown in FIG. 3, then the densities and the temperature may also be recovered in three dimensions by a Radon transform, similar to what is used in computer tomography. Such a system can recover the temperature distribution in three dimensions within a hot gas (or a flame). It can also, which will be more important, simultaneously recover the three dimensional density distribution of each detectable molecular specie. These measurements are also performed without any physical probe since the radio signal may, as indeed was the case in our pilot experiment, that will be described penetrate through the ceramic wall of the chimney.

In the apparatus shown in FIG. 2, an experiment was carried out. An oxy/oil burner was installed and was burning in a steady state.

Figure 4:
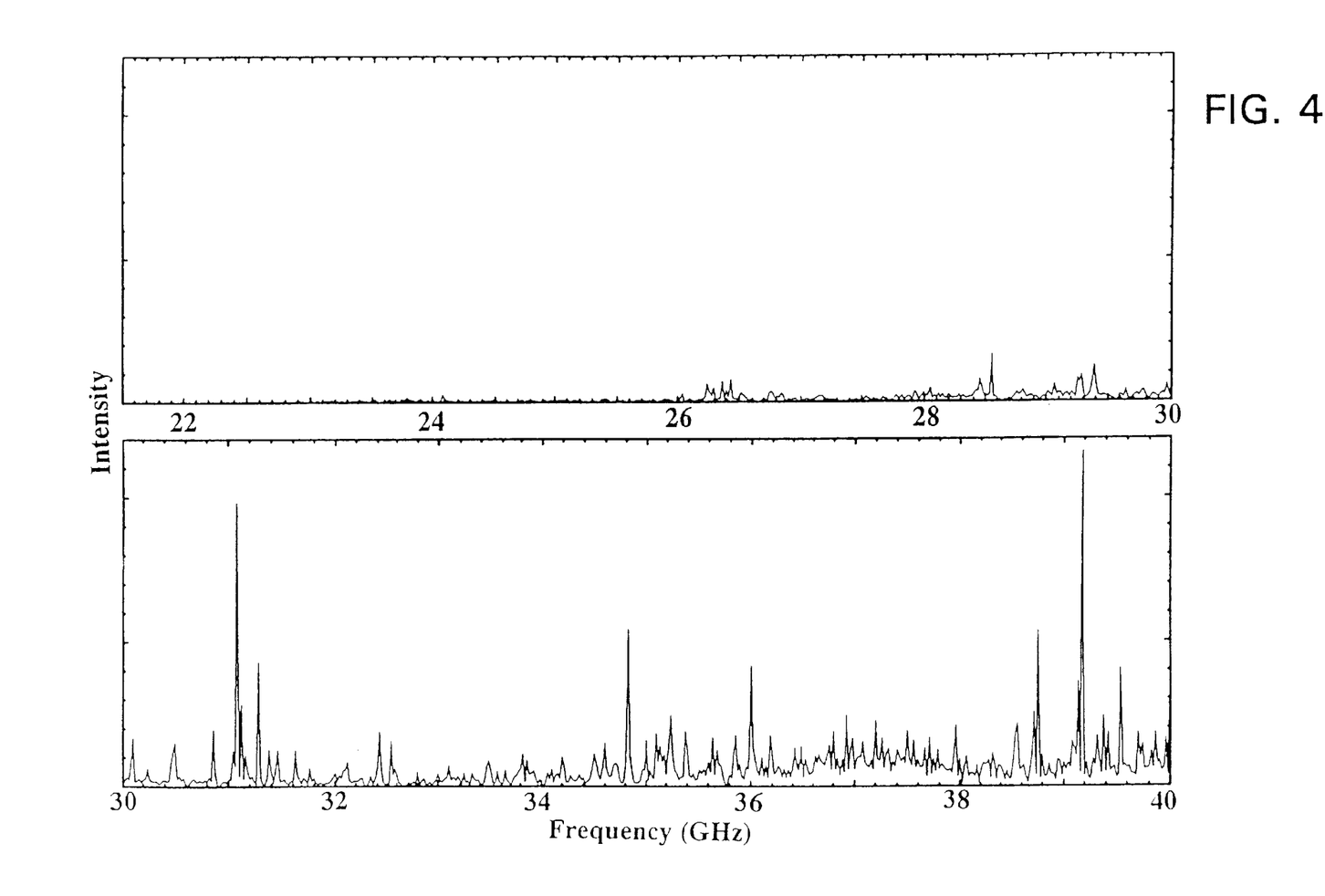
FIG. 4 is a representation of a spectrum observed in the radio band of 20–40 GHz in a chimney.
Figure 5:
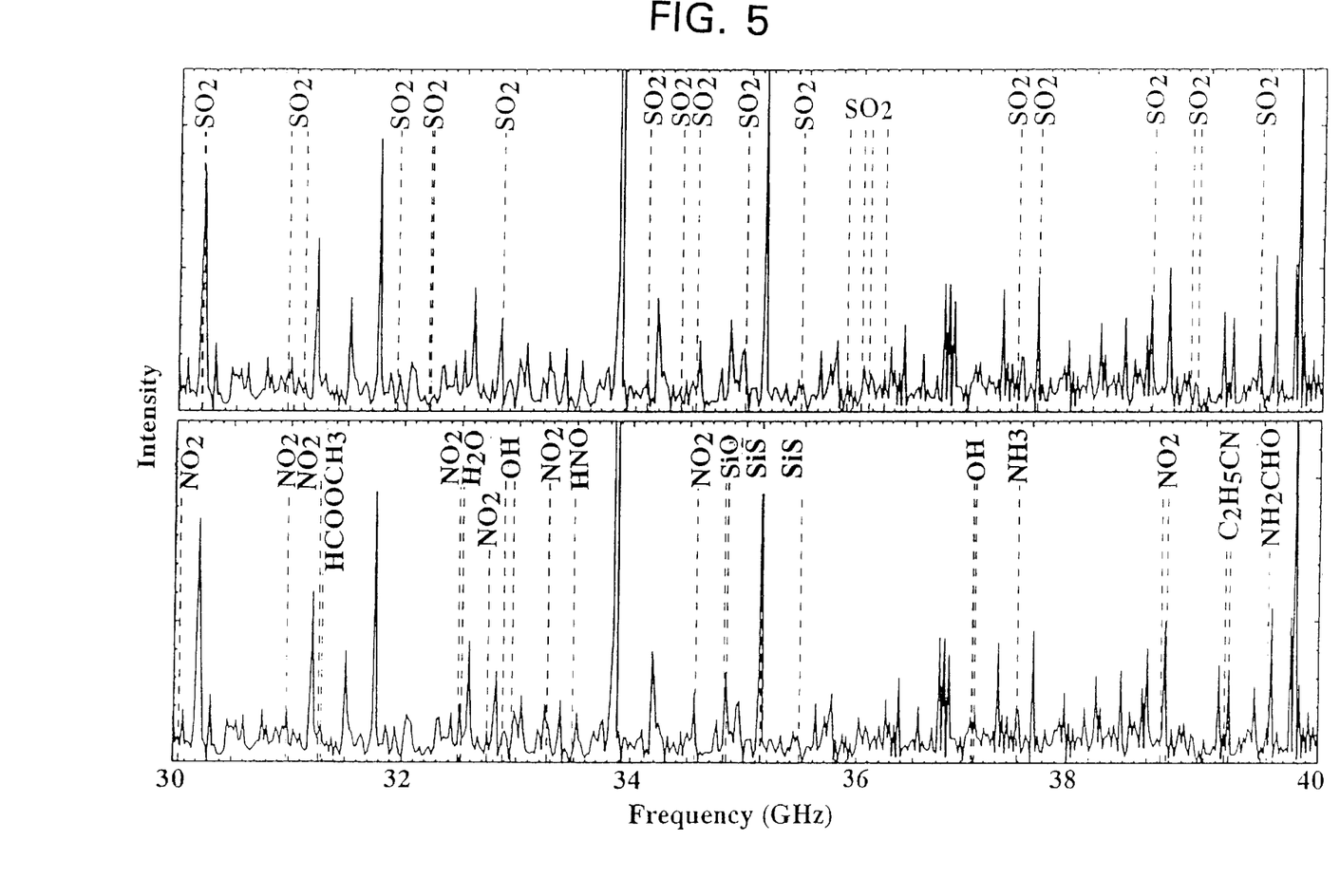
FIG. 5 illustrates the determination of gaseous components from the radio band spectrum.

FIG. 4 shows the spectrum observed in the radioband 20–40 GHz through the flow in the chimney. Most of these lines come from $SO_2$, some others from $NH_3$ and other molecules. It is therefore clearly possible to detect molecules within the radioband in gas flows on earth. As a consequence it is then also possible to make images of such a flow. FIG. 5 shows the identifications of some of the lines from one observations. Using $SO_2$ as a tracer it was possible to determine the temperature as well as the density of $SO_2$ as function of time.

An actual working example of the invention has been carried out, wherein, referring to FIG. 1, the following components were employed:

| | An actual working example of the invention has been carried out, wherein, referring to FIG. 1, the following components were employed: | |
|---|---|---|
| 12 | opening for oil-burner | |
| 13 | window through steel cover | Chrome-magnesite and Chamotte |
| 14 | transmitting antenna | 1.2 m diameter offset parabola from Parabolic AB |
| | rectangular feed horn | Quasar Technology for 26–40 Ghz band |
| | converter waveguide to coaxial cable | Quasar Technology for 26–30 GHz band |
| 15 | receiving antenna | 1.2 m diameter offset parabola from Parabolic AB |
| | rectangular feed horn | Quasar Technology for 26–40 Ghz band |
| | converter waveguide to coaxial cable | Quasar Technology for 26–30 Ghz band |
| 16 | signal generator | Wiltron System Signal Source type 360SS69 |
| 17 | receiver | Wiltron Active Device Test Set type 3621A |
| 18 | data acquisition | Wiltron Vector Network Analyser type 360B |
| 19 | data storage | PC computer with GPIB Interface |

Addresses for these companies are as follows:

Quasar Microwave Technology Ltd
Battle Road, Heathfield, Newton Abbot
Devon TQ12 6XU
United Kingdom Wiltron Company
490 Jarvis Drive
Morgan Hill, Calif. 95037-2809
USA Parabolic AB
Box 10257
S-434 23 Kungsbacka
Sweden As for the inter-unit connections, the radio frequency output of the transmitter 16 is connected to a power divider type Wiltron K24OC with a steel semirigid coaxial cable of 30 cm in length. The two output signals from the power divider are connected to the transmitting antenna 14 and the receiver 17 with steel coaxial cables. The other radio frequency port of the receiver 17 is connected to the receiving antenna 15. The data acquisition system 18 is connected to the transmitter 16 and the receiver 17 via GPIB bus cables. The computer 19 is also connected using a GPIB interface.

The data acquisition unit 18, i.e., the Vector Network Analyser, was set to step in 501 frequency steps between 30 and 40 Ghz and the division of the amplitudes of the received signal and the reference signal from the transmitter were stored for each frequency channel. A total integration time of 10 secs. was used for each frequency spectrum.

The data was stored on computer discs and each spectrum was then analyzed off line with a special computer program. A theoretical description of the analysis of molecular densities and temperatures can be found in "Microwave Spectroscopy": C. H. Townes and A. L. Schawlow, Dover Publications Inc. New York, ISBN 0-486-61798-X, which publication is hereby expressly incorporated by reference herein.

Figure 6:
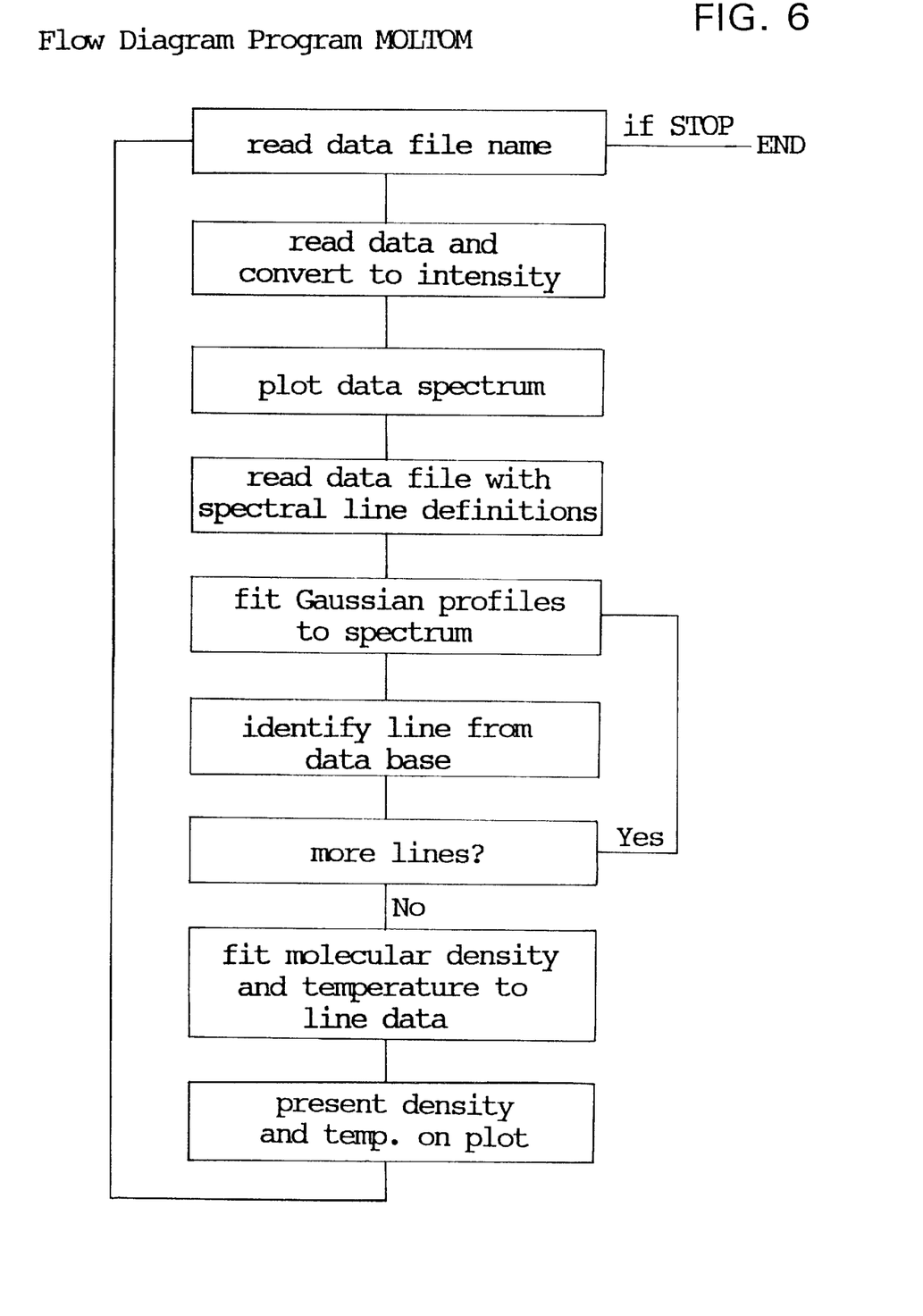
FIG. 6 is a flow diagram illustrating the sequence of steps performed by a computer program "MOLTOM5" set forth hereinbelow.

The computer program used is referred to internally as "MOLTOM5" and is illustrated in the form of a flow diagram shown in FIG. 6.

The actual computer program "MOLTOM5" is set forth immediately below. "MOLTOM5" and another computer program referred to internally as "SLAGG" make subroutine calls to four commercially available software packages. [The computer program "SLAGG" is more particularly utilized in conjunction with the invention disclosed in published International Application No. PCT/SE94/00099 (which corresponds to Swedish Patent Application No. 9300348-1).] These four commercially available software packages are:

PGPLOT from Dr. Tim Pearson, California Institute of Technology, Pasadena, Calif.;

LMSTR1 and GETERR from the Astronomical Image Processing System (AIPS) of National Radio Astronomy Observatory (NRAO), Socorro, N. Mex.; and SVDFIT from Numerical Recipes, Press, Flannery, Teukolsky and Vetterling, Cambridge University Press, isbn 0 521 30811 9.

Each of the four commercial software packages referred to immediately above is hereby expressly incorporated by reference herein.

The "MOLTOM5" computer program used in the above-described working example is as follows:

```
      PROGRAM MOLTOM5
C
      INTEGER IS,PGBEGIN
      Integer*2 status.dummy
      character*15 frame1,frame2,frame3
      character*128 record
      character*80 title
      character*16 mol
      REAL*4 FR1(512), AMP1(512), PH1(512)
      REAL*4 FR2(512), AMP2(512), PH2(512)
      REAL*4 FR3(512), AMP3(512), PH3(512)
      REAL*4 FR4(1024), AMP4(1024), x1(2), y1(2)
      REAL*4 xmin, ymin, ymax, fleal, flmag,
     *   tpl, x, ampsum, xnv(2), xv(2), xnvl(2), xnvh(2)
      integer gfunc, lpvl(12)
      external glunc
      REAL*4 xb(2), yb(2)
      real*8 data(1024), xtr(1024), enorm, dpar
      real*8 palms(12), ljac(12, 12), work(2148),
     *      lvec(2048), tol, sparms(12), tnorm
C
      REAL*4 X01(500), Y01(500)
      INTEGER NP01
C******************************************************************
            integer       pd,CDAT,DMAX,NWMAX
c
            parameter  (CDAT=2048, DMAX=21, NWMAX=10)
c
            real       I(CDAT+1.DMAX+1),v(DMAX+1,DMAX+1),w(DMAX+1)
      REAL SIGM(500)
            real      A01(DMAX)
      REAL      A(DMAX),B(DMAX)
c
            logical    accept,skip
c
      common /gdata/ data,xtr
C
      data clight/299792.0e0/
c      -------------------------------------------------------------
C
C
      ler=pgbegln(0,'/MSOFT',1,1)
      open(unit=22,file='lbb\mollom.lll')
      open(unit=18,file='lbb\mollom7.prm')
      open(unit=23,file='lbb\mollom.tlm')
C       write(6,*) 'Input file name.'
900     read(18,'(A)',END=999) fname t
      IF(Iname1(1,4).sq.'slop') goto 999
C       write(6,*) 'Input ref. file name:'
```

-continued

```
        OPEN(UNIT=17, FILE=Iname1)
100       lead(17,2000) record
        If(record(1:9).ne.'FREQUENCY') goto 100
c         write(6,'(A)') record(1:30)
        tpl=2.0*3.1415265350d0
        xmin=999999999.99
        xmin=-xmin
        ymin=xmin
        ymax=-ymin
        IN=0
1         read(17,2000, end=10, err=1) record
        record(42:43)=' '
2000    format(A)
        Ind=Index(record, 'm')
        If(Ind.gt.0) record(ind:ind)=' '
        read(record, 1000, err=1, end=1) 1S, X, Y, Z
1000    FORMAT(13,3F15,0)
        If(is.it.1) goto 1
        IN=IN+1
        FR1(IN)=X
        AMP1(IN)=Y*10.0e0
        PH1(IN)=Z*lpl/360.0e0
c         write(6,*) ln, ls, x, y, z
        If(1S.eq.501) goto 10
        GOTO 1
10      CONTINUE
        close(unit=17)
        do 1=1.501
            If(xmin.gt.fr1)(i)) xmin=fr1(1)
            If(xmax.lt,fr1(1)) xmax=fr1(1)
            If(ymin.gt.amp1(1)) ymin=amp1(1)
            If(ymax.lt.amp1(1)) ymax=amp1(i)
        enddo
        if(xmin.lt.29.99) goto 900
        ymin=0.0
        ymax=120.0
c         xmin=30.0
c         xmax=40.0
c         write(6,*) xmin, xmax, ymin, ymax
c         call pgsls(1)
c         CALL PGSLW(5)
        call pgscl(1)
        CALL PGENV(XMIN, XMAX, YMIN, YMAX, 0, 0)
        call pgsci(3)
        CALL PGLINE(501, FR1, AMP1)
        open(unit-21, file='lbb\molton.dat')
        write(22, '(A)') fname1(1:16)
        il0=0
4       read(21, '(110.3, A, 2110.3)', end=40) xx, mol, eu, sui
            If(xx.it.1.0) goto 40
            x1(1)=xx
            x1(2)=xx
            do 1=1.501
                df=abs(lri(i)-xx)
                If(db.it.0.02) then
                    1x-1
                endif
            enddo
            yynax=ampi(ix)
            ii=1x-2
            jjx=1x
            do jx=1, 3
                Ii=11+1
                If(abs(amp1(ii)).gl.abs(yynax)) then
                    yynax=amp1(ii)
                    jjx=ii
                endif
            enddo
c             write(6,*) ix, jjx, yynax, amp1(ix), amp1(jjx)
            ix=jjx
            xstr=fr1(1x-2)
            xslp=fr1(1x+2)
            parms(1)=amp1(1x)
C             If(dabs(parms(1)).it.0.02) goto 4
C             xsgn=1.0
C             If(parms(1).it.0.0) then
C                 xsgn=-1.0
C                 parms(1)=-parms(1)
C             endif
```

-continued

```
              parms(2)=fr1(1x)
              parms(3)=0.020
              jj=0
              do 1=1.501
                  If(Ir1(1).ge.xstr.and.fr1(1).le.xstp) then
                      jj=jj+1
                      data(jj)=amp1(1)
                      If(yynax.gl.0.0.and.amp1(1).it.0.0) then
                          data(jj)=0.0d0
                      else if(yynax.it.0.0.and.amp1(1).gt.0.0) then
                          data(jj)=0.0d0
                      endif
C                     If(xsgn.it.0.0) then
C                         data(jj)=-data(jj)
C                     endif
                      xfr(jj)=fr1(1)
                  endif
              enddo
C             write(6,*) If.parms(1), parms(2), parms(3)
              do jjk=1.3
                  lol=1.0d-5
                  call Imstr1(gfunc, jj, 3, parms, fvec, fjac, 12, tol, info,
                       lpvt, work, 2108)
              enddo
              inpnts=jj
              fnorm=enorm(inpnts, ivec)
              call getorr(1, 1pvt, ijac, eparms, 3, jj, 12, 1norm, work, lol)
C             eparms(2)=eparms(2)*3.0d0
C             eparms(3)=eparms(3)*3.0d0
              dpar=parms(1)/eparms(1)
C             parms(1)=xsgn*parms(1)
              dfr=xx.parms(2)
              dfr=abs(dir)
              if(dpar.ge.3.0d0.and.dir.it.0.2) then
c                 if(dpar.ge.3.0d0.and.dir.it.0.02) then
                      If(eu.gt.0.0) then
                          xeu=eu*1.440e0
c                         dp=1.0e0
                          dp=2.0e0*parms(3)*1.06/parms(2)*clight*1.67
c                         dp=dp*dp
                          xnu=log(parms(1)*dp/parms(2)/sul/1.634/1.634)
c                         xnu=log(parms(1)/parms(2)/sul)
                          110=110+1
                          x01(110)-xeu
                          y01(110)=xnu
                          sigm(110)=
     *                        (log((parms(1)+eparms(1))*dp/
     *                            parms(2)/sul/1.634/1.634)-
     *                        log((parms(1)-eparms(1))*dp/
     *                            parms(2)/sul/1.634/1.634))/4.0e0
                      else
                          xeu=0.0e0
                          xnu=0.0e0
                      endif
                      write(22,3331) mol(1:8), xx, yynax, parms(1), eparms(1), parms(2),
     *                    eparms(2), parms(3), eparms(3), xnu, xeu
                      x1(1)=parms(2)
                      x1(2)=parms(2)
                      y1(1)=ymin
                      y1(2)=0.80*ymax
                      if(eu.gt.0.0) then
c                         call pgsls(2)
c                         CALL PGSLW(1)
                          call pgscf(2)
                          call pgline(2, x1, y1)
                      endif
                      x1(1)=xx
                      x1(2)=xx
                      y1(1)=0.80*ymax
                      y1(2)=0.03*tmax
c                     call pgsls(1)
c                     CALL PGSLW(3)
                      call pgscl(6)
                      call pgline(2, x1, y1)
                      y1(1)=0.84*ymax
                      call pgsci(2)
                      call pgptext(x1(1), y1(1), 90.0, 0.0, mol)
                  endif
 3331         formal(A, 2x, F12.5, 18.2, 18.2, '+/-', 17.2, 115.5, '+/-', 110.5,
```

-continued

```
                              4112.5)
C
                      goto 4
40                        CLOSE(UNIT=21)
                      np01=110
                      a01(1)=0.0
                      a01(2)=0.5
                      pd=2
                      mp=cdat+1
                      np=dmax+1
                      CALL SVDFIT(X01, Y01, SIGM, NP01, A01, PD, U, V, W, MP, NP, CHISQ)
                      trol=-1.0e0/a01(2)
                      xlol=exp(a01(1))*6916.978*((trol/300.0e0)**1.50e0)*1.0e+14
                      xlol2=a01(1)
                      write(22,*)'next', trol, xlol, xlol2
                      write(23,*) fname1(1:16), trol, xlol
                      write(title,2222) lname1(1:15), trol, xlol
    2222      format(A,'Trol=', 18.0, 'Kelvin', 'N(SO\d2\u)=', e12.4
        *                         *cm\U-2\d*)
                      call pgscl(1)
                      CALL PGLABEL('frequency (GHz)', 'amplitude', title)
                      GOTO 900
     999    CALL PGEND
                      write(22,*) 'slop'
                      close(unit=22)
                      close(unit=23)
C
                      STOP
                      END
                          SUBROUTINE GFUNC (M, N, parms, FVEC, fjrow, IFLAG)
C                                       Variables used as adjustable
C                                       array dimension specifiers
C                                       should be declared simply as
C                                       INTEGER
                      INTEGER M, N, LDFJAC, lflag
                      REAL*8 parms(N), FVEC(M), fjrow(N), x
                      real*8 data(1024), amp, pos, sig, xfr(1024), res2, tslg2, elact
                      common/gdata/data, xlr
C                     ----------
C                     If lFLAG = 1 calculated the functions at X and
C                     return this vector in FVEC. Do not alter FJAC.
                      (If(lflag.gf.f) goto 100
                      do ldata=1, m
                          amp=parms(1)
                          pos=patms(2)
                          slg=parms(3)
c                           slg=0.0250
                      res2=2.772d0*(xlt(ldata)-pos)**2
                      tslg2=sig**2
                      fvec(idata)=data(ldata)-amp*dexp(-1.d0*res2/tslg2)
                      enddo
                      goto 999
C                     If lFLAG = 2 calculate the Jacobian at X and
C                     return this matrix in FJAC. Do not alter FVEC.
100                       continue
                          x=xfr(iflag-1)
                          amp=parms(1)
                          pos=parms(2)
                          slg=parms(3)
c                           slg=0.0250
                      res2=2.772d0*(x-pos)**2
                      tslg=slg**2
                      elact=dexp(-1.0d0*res2/tslg2)
                      fjrow(1)=efact
                      fjrow(2)=-5.544d0*amp'efact*(x-pos)/(slg*slg)
                      fjrow(3)=-2.d0*amp*efact*res2/(slg**3)
     999   continue
C                     ----------
                      RETURN
                      END
```

FIG. 6 illustrates in the form of a flow diagram the sequence of steps carried out by the above computer program "MOLTOM5".

The published PCT application to which the present U.S. application corresponds, namely PCT/SE94/00100, the published Swedish application from which it claims priority SE 9300347-3, as well as all documents cited in the International Search Report issued thereon, including U.S. Pat. No. 5,124,653 issued to Andresen et al. on Jun. 23, 1992, U.S. Pat. No. 4,693,614 issued to Hatono et al. on Sep. 15, 1987, U.S. Pat. No. 4,438,069 issued to Peterman et al. on Mar. 20, 1984 and Great Britain Patent 2030414 (and its U.S.

counterpart, U.S. Pat. No. 4,275,787, issued on Jun. 30, 1981), are hereby expressly incorporated by reference as if set forth in their entirety herein. Additionally, published PCT application PCT/SE94/00100 is directed to similar subject matter disclosed in published PCT application PCT/SE94/00099, which PCT application, the published Swedish application from which it claims Priority, SE 9300348-1, together with all documents cited in the International Search Report issued thereon, namely U.S. Pat. No. 4,737,791 issued to Jean et al., U.S. Pat. No. 5,115,242 issued to Nagamune et al., German Auslegeschrift 28 12 871 (and its U.S. counterpart U.S. Pat. No. 4,210,023, issued on Jul. 1, 1980) and European Patent No. 0060597 (and its U.S. counterpart, U.S. Pat. No. 4,458,530, issued on Jul. 10, 1984), are also hereby expressly incorporated by reference into the present application.

One feature of the invention resides broadly in a method for measuring temperature, molecular composition or molecular densities or any combination thereof in gases and/or flames in melting and/or combustion processes, characterized in that it comprises measuring electromagnetic radiation in the radio range defined as wavelengths between 30 micrometers and 500 meters with a radio antenna positioned outside a process room and/or exhaust channel, performing the measurements during a continuous melting and/or combustion process, and measuring spectral lines emitted by the high temperature collision excited molecules, and absorbed from a background signal when the population of energy levels for the collision excited molecule permits this.

Another feature of the invention resides broadly in a metal characterized in that molecular species are identified from the measured spectrum by comparing the detected spectral lines with molecular lines from an identification data base.

Yet another feature of the invention resides broadly in a method characterized in that the temperature is measured inside the process room and/or exhaust channel by measuring the relative intensities of several lines from the same molecular specie and comparing with a theoretical relation calculated for the expected population of energy levels as a function of temperature.

Still another feature of the invention resides broadly in a method characterized in that the density of the molecular species are determined by measuring the absolute intensity of a spectral line from that specie and compare with the theoretically expected intensity for the already determined temperature.

Another feature of the invention resides broadly in a method characterized in that the electromagnetic radiation is measured in narrow frequency channels resulting in a frequency spectrum which is compared with a known reference signal and is calibrated against the back of the process room and/or exhaust channel transmitted copy of the reference signal.

Yet another feature of the invention resides broadly in a method characterized in that the reference and background signal is created in steps of narrow frequency channels by stepping a signal generator in frequency.

Still another feature of the invention resides broadly in a method characterized in that the receiving antenna is an interferometer and that the two dimensional distribution of densities and temperature are reconstructed from the cross correlation of the signal of the individual interferometer elements.

Another feature of the invention resides broadly in a method characterized in that the signal is received simultaneously by interferometers placed at several azimuth angles around the processroom and/or exhaust channel and the three dimensional distribution of densities and temperature are reconstructed by projections.

The components disclosed in the various publications, disclosed or incorporated by reference herein, may be used in the embodiments of the present invention, as well as, equivalents thereof.

The appended drawings in their entirety, including all dimensions, proportions and/or shapes in at least one embodiment of the invention, are accurate and to scale and are hereby included by reference into this specification.

All, or substantially all, of the components and methods of the various embodiments may be used with at least one embodiment or all of the embodiments, if more than one embodiment is described herein.

All of the patents, patent applications and publications recited herein are hereby incorporated by reference as if set forth in their entirety herein.

The corresponding foreign and international patent publication applications, namely, Swedish Patent Application No. 9300347-3, filed on Feb. 3, 1993, and PCT/SE94/00100, filed on Feb. 3, 1994, having inventor Lars Bååth, and SE-OS 9300347-3 and SE-PS 9300347-3 and International Application No. PCT/SE94/00100, and International Publication No. WO94/18550, are hereby incorporated by reference as is set forth in their entirety herein.

The invention as described hereinabove in the context of the preferred embodiments is not to be taken as limited to all of the provided details thereof, since modifications and variations thereof may be made without departing from the spirit and scope of the invention.

What is claimed is:

1. A method for measuring a molecular composition of at least one molecular species of at least one of:

a gas, and a flame in a combustion process, said method comprising the steps of:

storing a quantity representative of at least one spectral line which at least one spectral line corresponds to at least one known molecular composition of the at least one of a gas and a flame in a combustion process;

positioning a transmitter;

the transmitter being configured to transmit radio waves;

positioning a receiver to receive radio waves from the transmitter;

disposing the transmitter and the receiver on opposite sides of a process chamber or exhaust channel;

transmitting a signal from the transmitter through the process chamber or exhaust channel;

receiving a modified signal with at least one spectral line through the process chamber or exhaust channel with the receiver;

comparing the received modified signal to the transmitted signal and determining at least one present spectral line in said modified signal; and comparing the determined at least one spectral line to the stored at least one spectral line, and determining the molecular composition of the at least one of a gas and a flame of said step of comparing the determined at least one spectral line to the stored at least one spectral line, and the stored at least one known molecular composition.

2. The method for measuring a molecular composition of at least one molecular species of at least one of a gas and a flame in a combustion process according to claim 1, wherein said step of transmitting a signal further comprises the step of transmitting a radio wave with a wavelength between 500 meters and 30 micrometers.

3. The method for measuring a molecular composition of at least one molecular species of at least one of a gas and a flame in a combustion process according to claim 2, wherein a step of measuring an intensity of electromagnetic radiation emitted by high temperature collision excited molecules present in the at least one of a gas and flame is included after said modified signal is received.

4. The method for measuring a molecular composition of at least one molecular species of at least one of a gas and a flame in a combustion process according to claim 3, wherein said step of comparing the received signal to the transmitted signal further comprises the step of filtering out the transmitted signal from the received signal and obtaining the determined at least one spectral line.

5. The method for measuring a molecular composition of at least one molecular species of at least one of a gas and a flame in a combustion process according to claim 4, wherein:
   the transmitter comprises a signal generator; and
   said step of transmitting a signal further comprises the step of stepping the signal generator in steps comprising narrow frequency channels over a wide frequency band and generator the transmitted signal;
   each of said narrow frequency channels being substantially smaller than said wide frequency band.

6. The method for measuring a molecular composition of at least one molecular species of at least one of a gas and a flame in a combustion process according to claim 5, further comprising the step of obtaining a reference signal by transmitting a signal to the receiver when the process channel or exhaust chamber is empty.

7. The method for measuring a molecular composition of at least one molecular species of at least one of a gas and a flame in a combustion process according to claim 6, wherein:
   said step of receiving the modified signal further comprises the step of calibrating the received by using the reference signal corresponding to the received modified signal near its at least one spectral line;
   the measured intensity of electromagnetic radiation being related to the determined at least one spectral line;
   said step of determining the composition comprises:
      determining the temperature of the at least one of a gas and flame by using a theoretical relation between measured intensities of the determined plurality of spectral lines and the temperature to be determined; and
      determining the molecular density of at least one molecular species of the at least one of a gas and flame by measuring the absolute intensity of said determined at least one spectral line, and using a comparison between the measured intensity of the determined at least one spectral line and the theoretically expected intensity corresponding to the determined temperature;
   said step of determining at least one spectral line further comprises the step of determining a plurality of spectral lines;
   said step of determining a plurality of spectral lines further comprises the step of searching a database for known spectral lines which coincide in frequency with the determined plurality of spectral lines;
   said step of comparing the determined at least one spectral line further comprises the step of applying a Gaussian model fit to the determined plurality of spectral lines and determining at least one of amplitude, frequency and line width of the determined plurality of spectral lines and calibrating the determined at least one of amplitude, frequency and line width of the determined plurality of spectral lines to a known temperature;
   said step of comparing the determined at least one spectral line further comprises the step of comparing with a computer the determined plurality of spectral lines to the stored at least one spectral line;
   said receiver comprises a plurality of interferometers;
   said method further comprises the step of determining a two dimensional distribution of molecular composition and temperature to determine the composition to be measured;
   said step of determining a two dimensional distribution further comprises the step of cross correlating individual signals from the plurality of interferometers; and
   said method further comprises the step of positioning said plurality of interferometers at azimuth angles about the process chamber or exhaust channel to receive the transmitted signal and then determining a three dimensional distribution of molecular composition and temperature by using a Radon transform to determine the temperature to be measured.

8. A method for measuring a molecular composition of at least one molecular species of at least one of:
   a gas from a combustion process, which gas is not in combustion, and
   a flame in a combustion process,
   said method using a measuring system for measuring the molecular composition, and said method comprising the steps of:
   storing a quantity representative of at least one spectral line which at least one spectral line corresponds to at least one known molecular composition of the at least one molecular species of at least one of:
      a gas from a combustion process, which gas is not in combustion, and
      a flame in a combustion process;
   positioning a transmitter;
   the transmitter being configured to transmit radio waves;
   positioning a receiver to receive radio waves from the transmitter;
   disposing the transmitter and the receiver on opposite sides of a chimney;
   receiving a reference signal by transmitting a signal to the receiver from the transmitter when the chimney does not contain the at least one of:
      a gas from a combustion process, which gas is not in combustion; and
      a flame in a combustion process;
   calibrating the measuring system with said received reference signal;
   transmitting a signal from the transmitter through the chimney when the chimney contains the at least one of:
      a gas from a combustion process, which gas is not in combustion, and
      a flame in a combustion process;
   receiving a modified signal with at least one spectral line through the chimney with the receiver when the chimney contains the at least one of:
      a gas from a combustion process, which gas is not in combustion, and a flame in a combustion process;
comparing the received modified signal with at least one spectral line to the previously received reference signal and determining at least one present spectral line in said received modified signal; and
comparing the determined at least one spectral line to the stored quantity representative of at least one spectral line, and determining the molecular composition of the at least one molecular species of the at least one of:
    a gas from a combustion process, which gas is not in combustion, and
    a flame in a combustion process,
in the chimney from a result of said step of comparing the determined at least one spectral line to the stored quantity representative of at least one spectral line and the corresponding at least one known molecular composition.

9. The method for measuring a molecular composition of at least one molecular species of at least one of a gas from a combustion process, which gas is not in combustion, and a flame in a combustion process according to claim 8, wherein said step of transmitting a signal further comprises the step of transmitting a radio wave with a wavelength between 500 meters and 30 micrometers.

10. The method for measuring a molecular composition of at least one molecular species of at least one of a gas from a combustion process, which gas is not in combustion, and a flame in a combustion process according to claim 8, wherein a step of measuring an intensity of electromagnetic radiation emitted by high temperature collision excited molecules present in the at least one of a gas and flame is included after said modified signal is received.

11. The method for measuring a molecular composition of at least one molecular species of at least one of a gas from a combustion process, which gas is not in combustion, and a flame in a combustion process according to claim 10, wherein said step of comparing the received modified signal to the reference signal further comprises the step of filtering out the transmitted signal from the received signal and obtaining the determined at least one spectral line.

12. The method for measuring a molecular composition of at least one molecular species of at least one of a gas from a combustion process, which gas is not in combustion, and a flame in a combustion process according to claim 11, wherein:
    the transmitter comprises a signal generator; and
    said step of transmitting a signal further comprises the step of stepping the signal generator in steps comprising narrow frequency channels over a wide frequency band and generator the transmitted signal;
    each of said narrow frequency channels being substantially smaller than said wide frequency band.

13. The method for measuring a molecular composition of at least one molecular species of at least one of a gas from a combustion process, which gas is not in combustion, and a flame in a combustion process according to claim 12, further comprising:
    the measured intensity of electromagnetic radiation being related to the determined at least one spectral line; and
    said step of determining the molecular composition comprises:
        determining the temperature of the at least one of a gas and flame by using a theoretical relation between measured intensities of the determined plurality of spectral lines and the temperature to be determined; and
        determining the molecular density of at least one molecular species of the at least one of a gas and flame by measuring the absolute intensity of said determined at least one spectral line, and using a comparison between the measured intensity of the determined at least one spectral line and the theoretically expected intensity corresponding to the determined temperature.

14. The method for measuring a molecular composition of at least one molecular species of at least one of a gas from a combustion process, which gas is not in combustion, and a flame in a combustion process according to claim 13, wherein:
    said step of determining at least one spectral line further comprises the step of determining a plurality of spectral lines;
    said step of determining a plurality of spectral lines further comprises the step of searching a database for known spectral lines which coincide in frequency with the determined plurality of spectral lines.

15. The method for measuring a molecular composition of at least one molecular species of at least one of a gas from a combustion process, which gas is not in combustion, and a flame in a combustion process according to claim 14, wherein said step of comparing the determined at least one spectral line further comprises the step of applying a Gaussian model fit to the determined plurality of spectral lines and determining at least one of amplitude, frequency and line width of the determined plurality of spectral lines and calibrating the determined at least one of amplitude, frequency and line width of the determined plurality of spectral lines to a known temperature.

16. The method for measuring a molecular composition of at least one molecular species of at least one of a gas from a combustion process, which gas is not in combustion, and a flame in a combustion process according to claim 15, wherein said step of comparing the determined at least one spectral line further comprises the step of comparing with a computer the determined plurality of spectral lines to the stored at least one spectral line.

17. The method for measuring a molecular composition of at least one molecular species of at least one of a gas from a combustion process, which gas is not in combustion, and a flame in a combustion process according to claim 16, wherein:
    said receiver comprises a plurality of interferometers; and
    said method further comprises the step of determining a two dimensional distribution of molecular composition and temperature to determine the molecular composition to be measured.

18. The method for measuring a molecular composition of at least one molecular species of at least one of a gas from a combustion process, which gas is not in combustion, and a flame in a combustion process according to claim 17, wherein said step of determining a two dimensional distribution further comprises the step of cross correlating individual signals from the plurality of interferometers.

19. The method for measuring a molecular composition of at least one molecular species of at least one of a gas from a combustion process, which gas is not in combustion, and a flame in a combustion process according to claim 18, further comprising the step of positioning said plurality of interferometers at azimuth angles about the chimney to receive the transmitted signal and then determining a three dimensional distribution of molecular composition and temperature by using a Radon transform to determine the temperature to be measured.

20. A method for measuring a molecular composition and at least one of a temperature or a molecular density of at least one molecular species of at least one of:

a gas, and a flame in a combustion process, said method comprising the steps of:

storing a quantity representative of at least one spectral line which at least one spectral line corresponds to at least one known molecular composition and at least one of at least one known temperature or at least one known molecular density of at least one of a gas and a flame in a combustion process;

positioning a transmitter;

the transmitter being configured to transmit radio waves;

positioning a receiver to receive radio waves from the transmitter;

disposing the transmitter and the receiver on opposite sides of a process chamber or exhaust channel;

transmitting a signal from the transmitter through the process chamber or exhaust channel;

receiving a modified signal with at least one spectral line through the process chamber or exhaust channel with the receiver;

comparing the received modified signal to the transmitted signal and determining at least one present spectral line in said modified signal; and     comparing the determined at least one spectral line to the stored at least one spectral line, and determining the molecular composition and at least one of the temperature or molecular density of the at least one of a gas and a flame in the process chamber or exhaust channel from a result of said step of comparing the determined at least one spectral line to the stored at least one spectral line, and the stored at least one known composition and at least one of the stored at least one known temperature or the stored at least one known molecular density.

* * * * *